(12) United States Patent
Barton et al.

(10) Patent No.: US 9,938,226 B2
(45) Date of Patent: Apr. 10, 2018

(54) GAS PHASE PRODUCTION OF ALKYL ALKANOATE

(71) Applicant: Dow Global Technologies LLC, Midland, MI (US)

(72) Inventors: David G. Barton, Midland, MI (US); Gerolamo Budroni, Terneuzen (NL); Steven L. F. Corthals, Wachtebeke (BE)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 15/022,639

(22) PCT Filed: Sep. 11, 2014

(86) PCT No.: PCT/US2014/055064
§ 371 (c)(1),
(2) Date: Mar. 17, 2016

(87) PCT Pub. No.: WO2015/047735
PCT Pub. Date: Apr. 2, 2015

(65) Prior Publication Data
US 2016/0229788 A1 Aug. 11, 2016

Related U.S. Application Data

(60) Provisional application No. 61/884,187, filed on Sep. 30, 2013.

(51) Int. Cl.
| | | |
|---|---|---|
| C07C 67/343 | (2006.01) | |
| C07C 67/38 | (2006.01) | |
| B01J 27/043 | (2006.01) | |
| B01J 27/045 | (2006.01) | |

(52) U.S. Cl.
CPC .......... *C07C 67/343* (2013.01); *B01J 27/043* (2013.01); *B01J 27/045* (2013.01); *C07C 67/38* (2013.01)

(58) Field of Classification Search
None
See application file for complete search history.

(56) References Cited

U.S. PATENT DOCUMENTS

| | | | |
|---|---|---|---|
| 2,593,440 A * | 4/1952 | Hagemeyer, Jr. | ........ B01J 27/06 560/232 |
| 3,507,891 A | 4/1970 | Hearne et al. | |
| 3,935,228 A | 1/1976 | Keblys | |
| 4,628,113 A | 12/1986 | Current | |
| 6,284,919 B1 | 9/2001 | Pearson et al. | |
| 2012/0078012 A1* | 3/2012 | Torrence | ................. C07C 51/44 562/519 |

FOREIGN PATENT DOCUMENTS

| | | |
|---|---|---|
| CN | 102775302 A | 11/2012 |
| DE | 240005 A1 | 10/1986 |
| DE | 240006 A1 | 10/1986 |
| EP | 0310168 A2 | 4/1989 |
| EP | 0321054 A2 | 6/1989 |
| EP | 0411721 B1 | 12/1994 |
| EP | 0495548 B1 | 9/1995 |
| WO | 96/19434 A1 | 6/1996 |
| WO | 98/41495 A1 | 9/1998 |
| WO | 99/21820 A1 | 5/1999 |
| WO | 99/36385 A1 | 7/1999 |
| WO | 2008/023338 A1 | 2/2008 |
| WO | 2011/073655 A1 | 6/2011 |

OTHER PUBLICATIONS

Matsuda et al., Bull. Chem Soc. Japan, vol. 38, No. 5, Jan. 1, 1965, pp. 710-715.
S.K. Bhattacharyya et al., Brennstoff Chemie, No. 4, vol. 43, Oct. 3, 1961, pp. 1-14.
R.A.M. Robertson et al., Chem. Commun., 2001, pp. 47-48.
K. Yasuda et al., Bull. Chem. Soc. Jpn., 65, 1992, pp. 289-291.

* cited by examiner

*Primary Examiner* — Sudhakar Katakam
*Assistant Examiner* — Ana Z Muresan
(74) *Attorney, Agent, or Firm* — Husch Blackwell LLP

(57) ABSTRACT

Alkyl alkanoates, e.g., methyl propionate, are made by a gas phase process comprising the step of contacting under carbonylation conditions an alkene (e.g., ethylene), carbon monoxide, an alkanol (e.g., methanol), and a solid sulfide-based metal catalyst (e.g., iron sulfide). The alkyl alkanoate can be converted in a second step to an alkyl ester of an aliphatic carboxylic acid, e.g., methyl methacrylate, through condensation with an aldehyde, e.g., formaldehyde.

11 Claims, No Drawings

GAS PHASE PRODUCTION OF ALKYL ALKANOATE

FIELD OF THE INVENTION

This invention relates to the gas phase production of alkyl alkanoates. In one aspect the invention is the gas-phase production of alkyl alkanoates by the carbonylation of an alkene with an alkanol using a heterogeneous sulfide-based metal catalyst.

BACKGROUND OF THE INVENTION

Various methods are known for the production of alkyl esters of aliphatic carboxylic acids, e.g., methyl methacrylate (MMA). One commercial method relies solely on acetone cyanohydrin (ACH) technology, i.e., the reaction of acetone with hydrogen cyanide to form ACH followed by acid-assisted hydrolysis and esterification with methanol to produce approximately 400 kilo-tons annually of MMA. Although the ACH route has traditionally been a core technology used in the United States and other parts of the world, lower cost alternative technologies are under consideration for future capacity increases. Several of these alternative technologies are ethylene-based. One such method is the hydroformylation of ethylene-to-propionaldehyde, followed by condensation to form methacrolein (MA) and subsequent oxidation and esterification to form MMA. Another route is the Alpha process that is commercially practiced by Lucite (currently owned by Mitsubishi Rayon). This is a two-step, liquid phase process that uses a homogeneous palladium-based catalyst to make methyl propionate which is then condensed with formaldehyde in a second step to make MMA. The process is described in WO 1999/021820. Other reports of homogenous catalysts for the liquid phase carbonylation of ethylene to methyl propionate include U.S. Pat. No. 3,507,891 (cobalt-pyridine catalyst), *Chem. Commun.*, 2001, 47-48 (rhodium/b-ketophosphine catalyst); and *J. Molecular Catalysis* 40 (1987) 243-254, Hidai et al. (ruthenium-iodide catalyst).

One report of a heterogeneous catalyst that operates in the gas phase is by Bhattacharyya, S. K. and Nag, S. N., *Brennstoff-Chemie*, Vol. 43, p. 114-118 (1962). This work describes the use of metal iodides supported on silica gel for the synthesis of methyl propionate from ethylene, CO, and methanol in the gas phase. This process produces a large amount of undesirable by-product oxygenates and hydrocarbon compounds, and operates at a pressure of 253 bar (25.3 MPa).

SUMMARY OF THE INVENTION

In one embodiment the invention is a process comprising the step of contacting under carbonylation conditions an alkene gas, carbon monoxide gas, an alkanol gas and a solid sulfide-based metal catalyst to produce an alkyl alkanoate.

In one embodiment the invention is a process comprising the step of contacting under halogen-free carbonylation conditions an alkene gas, carbon monoxide gas, an alkanol gas and a solid sulfide-based metal catalyst to produce an alkyl alkanoate.

In one embodiment the invention is a process comprising the step of contacting under carbonylation conditions, ethylene gas, carbon monoxide gas, methanol gas and a solid sulfide-based metal catalyst to produce methyl propionate. In one embodiment the carbonylation conditions are halogen-free carbonylation conditions.

In one embodiment the invention is a two-step process comprising:
A. Contacting under carbonylation conditions an alkene gas, carbon monoxide gas, an alkanol gas, and a solid, sulfide-based metal catalyst to produce an alkyl alkanoate; and
B. Contacting under condensation conditions the alkyl alkanoate of Step A with an aldehyde to produce an alkyl ester of an aliphatic carboxylic acid.

In one embodiment the carbonylation conditions are halogen-free carbonylation conditions.

In one embodiment the invention is a two-step process comprising:
A. Contacting under carbonylation conditions ethylene gas, carbon monoxide gas, methanol gas, and a solid, sulfide-based metal catalyst to produce an methyl propionate; and
B. Contacting under condensation conditions the methyl alkanoate of Step A with formaldehyde to produce methyl methacrylate.

In one embodiment the carbonylation conditions are halogen-free carbonylation conditions.

DETAILED DESCRIPTION OF THE PREFERRED EMBODIMENT

Definitions

All references to the Periodic Table of the Elements refer to the Periodic Table of the Elements published at page 1-10 of the CRC Handbook of Chemistry and Physics, 71$^{st}$ Ed. (1990-1991). Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of synthetic techniques, product and processing designs, polymers, catalysts, definitions (to the extent not inconsistent with any definitions specifically provided in this disclosure), and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, weight percentages, etc., is from 100 to 1,000, then the intent is that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the amounts of the various reactants in and the operating conditions of the inventive process.

"Composition" and like terms mean a mixture or blend of two or more components.

"Carbonylation conditions" and like terms mean the temperature, pressure and other conditions necessary for an alkene, carbon monoxide and an alkanol, one or more of which is at least partially in the form of a gas, to react with one another over and in contact with a solid sulfide-based catalyst to form an alkyl alkanoate. In one embodiment each of the alkene, CO and alkanol are at least partially in the form of a gas. In one embodiment each of the alkene, CO and alkanol are completely or nearly completely in the form of a gas.

"Halogen-free carbonylation conditions" and like terms mean carbonylation conditions in which halogen in any form is absent or essentially absent from the space in which the alkene, CO and alkanol are contacted over a sulfide-based metal catalyst to form an alkyl alkanoate. "Essentially absent" means that any halogen present in the reaction space is present in an amount that does not materially affect the conversion or selectivity of the reactants to the desired alkyl alkanoate. The source of such halogen can be, for example, from one or more of the feeds to the reaction or the catalyst (as, for example, a contaminant), or from the surface of a piece of equipment, etc. In one embodiment "halogen-free" means less than (<)1000 parts per million (ppm), preferably <10 ppm and more preferably <1, ppm based on the combined weight of the reactants.

"Condensation conditions" and like terms mean the temperature, pressure and other conditions necessary for an alkyl alkanoate and an aldehyde, each in the form of a gas, to react with one another over and in contact with a solid condensation catalyst to form an alkyl ester of an aliphatic carboxylic acid.

Production of the Alkyl Alkanoate

Reactants

In one embodiment the invention is a process for the production of an alkyl alkanoate from alkene, carbon monoxide and alkanol. The alkene is of the formula $C_nH_{2n}$ in which n is an integer greater than (>) 1, typically 2-12 and more typically 2-8. Most typically and preferably n is 2, i.e., the alkene is ethylene.

The alkanol, i.e., alcohol, is typically a $C_{1-30}$ alkanol which may contain one or more substituents such as a cyano, carbonyl, alkoxy or aryl group. Illustrative alkanols include, but are not limited to, methanol, ethanol, propanol, 2-propanol, 2-butanol, t-butyl alcohol and capryl alcohol. For purposes of this invention, polyhydroxyl compounds such as diols and sugars, are considered alkanols that can be used in the practice of this invention. Methanol is the preferred alkanol.

The carbon monoxide can be used neat or in combination with one or more other gases that are inert with the reaction reagents, products and by-products under reaction conditions. These other gases include, but are not limited to, nitrogen, carbon dioxide and the noble gases.

Catalyst

The catalyst is a sulfide-based catalyst, particularly a metal sulfide catalyst. The catalyst can comprise one or more metals. Typically the catalyst comprises at least one Group VIII metal, e.g., iron, cobalt, nickel, rhodium, etc., and it can contain one or more other metals as well, e.g., a Group IA metal such as potassium or another transition metal such as titanium, vanadium, chromium, manganese, copper, zinc, tungsten and the like. The catalyst is a sulfide which means that at least one metal of the catalyst is bonded covalently or ionically to at least one sulfur atom. Typical and preferred catalysts for use in this invention include, but are not limited to, iron sulfide, cobalt sulfide, potassium rhodium sulfide and nickel sulfide.

Metal sulfides are well known in the art, and they can be prepared by various processes, e.g., precipitation/coprecipitation. For example cobalt sulfide can be prepared by precipitation of an aqueous solution of $(NH_4)_2S$ and an aqueous cobalt salt solution such as a cobalt nitrate solution. The precipitate is filtered, dried and treated in a furnace at, for example 500° C., under a nitrogen gas blanket. Purchased cobalt sulfides are also effective catalysts' such as, for example CAS 1317-42-6 available from such suppliers as Sigma Aldrich and Materion Process Conditions and Equipment The process of this invention is conducted in the gas phase over a solid catalyst. As such, the alkene, CO and alkanol are introduced as gases and contacted with one another over and in contact with a solid catalyst bed. The reactants can be introduced in a single or multiple feed streams. The molar ratio of CO to alkene is typically at least 1:1, typically at least 3:1, more typically from 3:1 to 50:1 and even more typically from 3:1 to 15:1. The molar ratio of alkene to alkanol is typically at least 0.1:1, more typically at least 0.5:1, more typically from 0.1:1 to 10:1 and even more typically from 0.2:1 to 2:1.

Although the process can be operated in either a continuous or batch mode, the process is typically and preferably operated in a continuous mode.

The process temperature is typically from 120° C. to 450° C., more typically from 250° C. to 380° C. and even more typically from 280° C. to 340° C. The total pressure of the process is typically from 0.1 to 20 MPa, more typically from 1.5 to 6 MPa. The space velocity of the process is typically from 100 to 1,000,000 liters of gas feed per liter of catalyst per hour (L/L*h), more typically from 500 to 5,000 L/L*hr.

In one embodiment the reaction is conducted in a high-pressure, fixed-bed reactor. In one embodiment the reactor is a tube reactor. In a typical protocol the temperature and pressure is slowly increased to the reaction conditions. The catalyst can be exposed to a feed consisting of an inert gas (such as nitrogen or helium), hydrogen, small amount of $H_2S$, carbon monoxide, olefins, alkanols and any combination of the above. The effluent gas from the reactor is analyzed via gas chromatography (GC) to determine product composition and amount of CO converted.

In one embodiment the reactor is a trickle bed reactor in which the catalyst is a solid and at least one of the reactants is at least partially in the gas phase. Typically, the alkene and carbon monoxide are completely gaseous but the alkanol, depending upon its boiling point and the carbonylation conditions, may be partially or totally liquid. For purposes of this invention, a process, such as that conducted in a trickle-bed reactor, is considered a gas phase process as long as at least one of the alkene, CO and alkanol is at least partially, preferably mostly and more preferably completely or near completely, in the gas phase. Typically in such a process, the alkene and CO are completely or near completely in the gaseous phase under carbonylation conditions.

In one embodiment of the invention, ethylene, CO and methanol are contacted at carbonylation conditions and over and in contact with a solid sulfide-based metal catalyst to form methyl propionate.

Production of Alkyl Esters of Aliphatic Carboxylic Acids

In one embodiment of the invention, the alkyl alkanoate made in the gas phase process described above is condensed with an aldehyde to form an alkyl ester of an aliphatic carboxylic acid. When the alkyl alkanoate is methyl propionate and the aldehyde is formaldehyde, the product is methyl methacrylate (MMA). The equipment, conditions and protocol of this condensation reaction are well known to those of skill in the art.

EXAMPLES

The gas phase carbonylation of ethylene with CO and methanol is observed in a series of tests performed in a fixed-bed, high pressure microreactor. Different metal sulfides (250 microliters) including iron sulfide, cobalt sulfide, potassium rhodium sulfide and nickel sulfide are tested at 5 MPa under a flow of carbon monoxide, methanol and ethylene (nitrogen is added as an internal standard) at different temperatures. Before the carbonylation tests the catalysts are exposed to syngas (containing 50 ppm of $H_2S$), syngas+ethylene, syngas+ethanol and syngas+methanol at temperatures between 270° C. and 330° C. The composition of the feed and the conditions tested are reported in Table 1 while the catalytic results are reported in Table 3.

TABLE 1

Reaction Conditions

| | CO | H2 | MeOH | C2H4 | N2 | SV, L/L*h | Temp, ° C. |
|---|---|---|---|---|---|---|---|
| Feed 1 | 72 | | 8 | 10 | 10 | 2800 | 290-330 |
| Feed 2 | 68 | 4 | 8 | 10 | 10 | 2800 | 290-330 |
| Feed 3 | 53 | | 20 | 13 | 14 | 2100 | 330 |

In a second experiment the test with the cobalt sulfide is performed using the feed described in Table 2 but this time before the carbonylation tests, the catalysts are exposed only to syngas containing 50 ppm of $H_2S$.

TABLE 2

Reaction Conditions

| | CO | H2 | MeOH | C2H4 | N2 | SV, L/L*h | Temp, ° C. |
|---|---|---|---|---|---|---|---|
| Feed 4 | 71 | | 8 | 11 | 10 | 3800 | 270-290-310 |
| Feed 5 | 21 | | 17 | 22 | 39 | 4000 | 290-310 |

The catalytic performances are described in Table 3. This table indicates the type of feed (as described in Tables 1 and 2), the type of the catalyst, the temperature (all reactions were performed at 5 MPa), and the performance of each catalyst. Specifically, for each catalyst is reported the conversion of methanol, ethylene and total carbon and the selectivity towards the main products detected. The formation of methyl propionate is observed for all the sulfides and selectivity of methyl propionate above 97% was observed. Metal sulfide catalysts activate selectively the gas phase alkoxy carbonylation reaction.

TABLE 3

Distribution of By-Products

| Cat. | Example | Feed | Temp. ° C. | Conv % Carbon | Conv % Ethylene | Conv % Methanol | Sel % Methyl Propionate | Sel % Acetaldehyde | Sel % Propionaldehyde | Sel % Ethyl Acetate | Sel % Methyl Acetate | Sel % Carbon dioxide | Sel % Ethanol + 1-Propanol | Sel % Methane + Ethane |
|---|---|---|---|---|---|---|---|---|---|---|---|---|---|---|
| CoS | 1 | Feed 1 | 290 | 9.2 | 15.4 | 36.0 | 71.2 | 0.9 | 1.7 | 0.5 | 13.0 | 4.7 | 0.3 | 6.2 |
| CoS | 1 | Feed 1 | 330 | 11.7 | 20.0 | 61.5 | 42.7 | 2.0 | 2.4 | 0.3 | 12.2 | 11.9 | 1.2 | 22.3 |
| CoS | 1 | Feed 2 | 290 | 9.5 | 22.8 | 27.8 | 64.3 | 1.3 | 6.4 | 0.4 | 5.6 | 2.2 | 4.5 | 12.2 |
| CoS | 1 | Feed 2 | 330 | 11.3 | 25.9 | 44.2 | 35.3 | 2.6 | 4.8 | 0.3 | 6.4 | 9.2 | 5.6 | 29.5 |
| CoS | 1 | Feed 3 | 330 | 33.9 | 45.0 | 81.4 | 20.7 | 3.1 | 1.3 | 0.5 | 7.5 | 22.6 | 1.5 | 36.0 |
| RhSK | 1 | Feed 1 | 290 | 2.6 | 3.4 | 56.4 | 4.8 | 4.0 | 6.0 | 1.6 | 6.0 | 20.5 | 28.5 | 23.7 |
| RhSK | 1 | Feed 2 | 290 | 2.1 | 3.1 | 36.2 | 4.8 | 4.0 | 9.5 | 1.6 | 8.3 | 19.4 | 24.6 | 26.2 |
| RhSK | 1 | Feed 2 | 330 | 3.4 | 8.1 | 88.5 | 1.8 | 2.3 | 6.1 | 0.9 | 0.7 | 10.9 | 30.4 | 37.6 |
| FeS | 1 | Feed 1 | 330 | 3.3 | 2.3 | 16.8 | 21.3 | 0.5 | 0.8 | 0.0 | 23.6 | 22.1 | 0.8 | 28.2 |
| FeS | 1 | Feed 2 | 290 | 1.7 | 1.1 | 3.3 | 37.4 | 0.9 | 2.8 | 0.0 | 8.4 | 7.9 | 1.4 | 39.3 |
| FeS | 1 | Feed 2 | 330 | 3.4 | 4.3 | 10.8 | 37.8 | 0.8 | 0.6 | 0.0 | 13.4 | 11.9 | 0.6 | 34.6 |
| FeS | 1 | Feed 3 | 330 | 7.4 | 4.0 | 19.2 | 17.9 | 0.5 | 0.7 | 0.9 | 16.3 | 24.8 | 2.1 | 32.6 |
| NiS | 1 | Feed 1 | 290 | 0.4 | 1.2 | 1.8 | 71.4 | 0.0 | 10.7 | 0.0 | 5.4 | 5.4 | 0.0 | 0.0 |
| NiS | 1 | Feed 1 | 330 | 0.7 | 1.5 | 2.3 | 38.5 | 5.8 | 11.5 | 0.0 | 5.8 | 4.8 | 0.0 | 18.3 |
| NiS | 1 | Feed 2 | 290 | 0.7 | 3.2 | 1.3 | 29.3 | 1.6 | 39.0 | 0.0 | 2.4 | 1.6 | 0.0 | 19.5 |
| NiS | 1 | Feed 3 | 330 | 1.3 | 5.8 | 5.4 | 31.1 | 9.7 | 5.8 | 0.0 | 5.8 | 4.9 | 0.0 | 15.5 |
| CoS | 2 | Feed 4 | 270 | 5.1 | 12.4 | 17.7 | 96.7 | 0.0 | 0.8 | 0.0 | 0.5 | 0.0 | 0.3 | 0.9 |
| CoS | 2 | Feed 4 | 310 | 26.3 | 55.5 | 78.6 | 95.4 | 0.0 | 0.3 | 0.0 | 2.4 | 0.0 | 0.1 | 1.0 |
| CoS | 2 | Feed 4 | 290 | 17.5 | 38.4 | 54.1 | 97.6 | 0.0 | 0.5 | 0.0 | 1.0 | 0.0 | 0.0 | 0.6 |
| CoS | 2 | Feed 5 | 290 | 25.6 | 24.7 | 34.9 | 90.8 | 0.3 | 1.5 | 0.0 | 1.3 | 0.0 | 0.2 | 5.1 |
| CoS | 2 | Feed 5 | 310 | 28.3 | 28.8 | 41.4 | 85.2 | 0.8 | 1.2 | 0.0 | 1.7 | 0.1 | 0.3 | 9.3 |
| RhS | 2 | Feed 4 | 290 | 3.5 | 10.6 | 11.7 | 56.5 | 1.0 | 7.8 | 0.0 | 5.0 | 0.0 | 1.2 | 27.2 |
| RhS | 2 | Feed 4 | 310 | 8.3 | 27.4 | 28.2 | 43.7 | 0.9 | 5.8 | 0.0 | 5.8 | 0.0 | 0.9 | 41.8 |

What is claimed is:

1. A gas phase process comprising the step of contacting under carbonylation conditions an alkene gas, carbon monoxide gas, an alkanol gas and a solid sulfide-based metal catalyst selected from the group consisting of iron sulfide, cobalt sulfide, potassium rhodium sulfide, nickel sulfide and combinations thereof to produce an alkyl alkanoate.

2. The process of claim 1 in which the alkene gas is of the formula $C_nH_{2n}$ in which n is from 2 to 12.

3. The process of claim 1 in which the carbonylation conditions are halogen-free.

4. The process of claim 1 in which the alkene gas is ethylene gas.

5. The process of claim 1 in which the alkanol comprises 1-30 carbon atoms.

6. The process of claim 1 in which the alkanol is methanol.

7. The process of claim 1 in which the carbonylation conditions include a temperature from 200° C. to 400° C. and a pressure from 0.1 MPa to 10 MPa.

8. The process of claim 1 conducted in a trickle-bed reactor.

9. A gas phase process comprising the step of contacting under carbonylation conditions ethylene gas, carbon monoxide gas, methanol gas and a solid sulfide-based metal catalyst selected from the group consisting of iron sulfide, cobalt sulfide, potassium rhodium sulfide, nickel sulfide and combinations thereof to produce methyl propionate.

10. The process of claim 9 comprising the further step of contacting under condensation conditions the methyl propionate with formaldehyde to produce an methyl methacrylate.

11. The process of claim 1 conducted in the absence of hydrogen.

* * * * *